United States Patent
Parris et al.

(10) Patent No.: US 9,494,550 B1
(45) Date of Patent: Nov. 15, 2016

(54) PROTECTED SENSOR FIELD EFFECT TRANSISTORS

(71) Applicants: Patrice M. Parris, Phoenix, AZ (US); Weize Chen, Phoenix, AZ (US); Richard J. de Souza, Chandler, AZ (US); Jose Fernandez Villasenor, Tokyo (JP); Md M. Hoque, Gilbert, AZ (US); David E. Niewolny, Austin, TX (US); Raymond M. Roop, Paradise Valley, AZ (US)

(72) Inventors: Patrice M. Parris, Phoenix, AZ (US); Weize Chen, Phoenix, AZ (US); Richard J. de Souza, Chandler, AZ (US); Jose Fernandez Villasenor, Tokyo (JP); Md M. Hoque, Gilbert, AZ (US); David E. Niewolny, Austin, TX (US); Raymond M. Roop, Paradise Valley, AZ (US)

(73) Assignee: Freescale Semiconductor, Inc., Austin, TX (US)

(*) Notice: Subject to any disclaimer, the term of this patent is extended or adjusted under 35 U.S.C. 154(b) by 0 days.

(21) Appl. No.: 14/731,795

(22) Filed: Jun. 5, 2015

(51) Int. Cl.
| | |
|---|---|
| *G01N 27/403* | (2006.01) |
| *G01N 27/414* | (2006.01) |
| *B01L 3/00* | (2006.01) |
| *H01L 21/67* | (2006.01) |
| *H01L 31/119* | (2006.01) |
| *H01L 29/66* | (2006.01) |

(52) U.S. Cl.
CPC ....... *G01N 27/414* (2013.01); *B01L 3/502715* (2013.01); *H01L 21/67259* (2013.01); *H01L 29/66431* (2013.01); *B01L 2200/10* (2013.01); *B01L 2200/12* (2013.01); *B01L 2300/041* (2013.01); *B01L 2300/0645* (2013.01); *B01L 2400/0418* (2013.01); *H01L 29/66462* (2013.01); *H01L 31/119* (2013.01)

(58) Field of Classification Search
CPC ........... G01N 27/414; B01L 3/502715; B01L 2200/10; B01L 2200/12; B01L 2300/041; B01L 2300/0645; B01L 2400/0418
USPC ....................................................... 257/253
See application file for complete search history.

(56) References Cited

U.S. PATENT DOCUMENTS

| | | | |
|---|---|---|---|
| 7,740,805 B2 | 6/2010 | Parris | |
| 8,263,336 B2 * | 9/2012 | Rothberg | ........... G01N 27/4145 257/253 |

(Continued)

OTHER PUBLICATIONS

Oki, A.; Adachi, S.; Takamura, Y.; Ishihara, K.; Ogawa, H.; Ichiki, T.; Horiike, Y., "Development of Elemental Technologies for Fabricating the Health Care Chip," *International Microprocesses and Nanotechnology Conference 2000*, Jul. 11-13, 2000, pp. 70-71.

(Continued)

*Primary Examiner* — Xinning Niu
*Assistant Examiner* — Vu A Vu

(57) ABSTRACT

Protected sensor field effect transistors (SFETs). The SFETs include a semiconductor substrate, a field effect transistor, and a sense electrode. The SFETs further include an analyte-receiving region that is supported by the semiconductor substrate, is in contact with the sense electrode, and is configured to receive an analyte fluid. The analyte-receiving region is at least partially enclosed. In some embodiments, the analyte-receiving region can be an enclosed analyte channel that extends between an analyte inlet and an analyte outlet. In these embodiments, the enclosed analyte channel extends such that the analyte inlet and the analyte outlet are spaced apart from the sense electrode. In some embodiments, the SFETs include a cover structure that at least partially encloses the analyte-receiving region and is formed from a cover material that is soluble within the analyte fluid. The methods include methods of manufacturing the SFETs.

18 Claims, 13 Drawing Sheets

(56) References Cited

U.S. PATENT DOCUMENTS

| | | | |
|---|---|---|---|
| 8,878,257 B2 | 11/2014 | Parris et al. | |
| 8,962,366 B2 * | 2/2015 | Putnam | G01N 27/414 438/49 |
| 2013/0153797 A1 * | 6/2013 | Puleo | B01L 3/50273 251/12 |
| 2014/0218727 A1 * | 8/2014 | Li | G01N 21/658 356/301 |
| 2014/0273191 A1 | 9/2014 | Tipgunlakant et al. | |
| 2015/0221541 A1 * | 8/2015 | Nemani | H01L 21/7682 438/666 |

OTHER PUBLICATIONS

Schasfoort, Richard B. M.; Schlautmann, Stefan; Hendrikse, Jan; Van Den Berg, Albert, "Field-Effect Flow Control for Microfabricated Fluidic Networks," *Science*, Oct. 29, 1999, pp. 942-945, vol. 286.

* cited by examiner

PROTECTED SENSOR FIELD EFFECT TRANSISTORS

FIELD

This disclosure relates generally to protected sensor field effect transistors and to methods of forming protected sensor field effect transistors.

BACKGROUND

Sensor field effect transistors (SFETs) are field effect transistors that can be utilized to detect a property, or parameter, of an analyte fluid that is brought into electrical contact with a gate of the sensor field effect transistor. Examples of such sensor field effect transistors include ion sensitive field effect transistors, ion selective field effect transistors, chemical sensitive field effect transistors, or biologically sensitive field effect transistors. Such SFETs generally include a sense electrode that changes potential (i.e., voltage) upon contact with the analyte fluid. The sense electrode is in electrical communication with the gate of the SFET, and changes in the electrical potential of the sense electrode cause changes in the electrical potential of the gate. This, in turn, causes a change in a resistance, or an electric current flow, between a source and a drain of the SFET, and this change in resistance, or electric current flow, can be quantified or can be correlated to the property or parameter of the analyte fluid.

SFETs can be sensitive to electronic drift, and this electronic drift generally is accounted for via calibration of the SFET prior to use. The calibration can take place as part of the manufacturing process (i.e., subsequent to manufacture of the SFET), at the point of distribution (i.e., prior to shipment of the SFET to an end user), or at the point of use (i.e. by the end user). Decreasing a potential for electronic drift of the SFET can decrease a need for calibration of the SFET at the point of use, thereby increasing convenience for the end user or accuracy of measurements performed by the SFET.

BRIEF DESCRIPTION OF THE DRAWINGS

The present invention is illustrated by way of example and is not limited by the accompanying Figures, in which like references indicate similar elements. Elements in the Figures are illustrated for simplicity and clarity and have not necessarily been drawn to scale.

DETAILED DESCRIPTION

Figure 1:
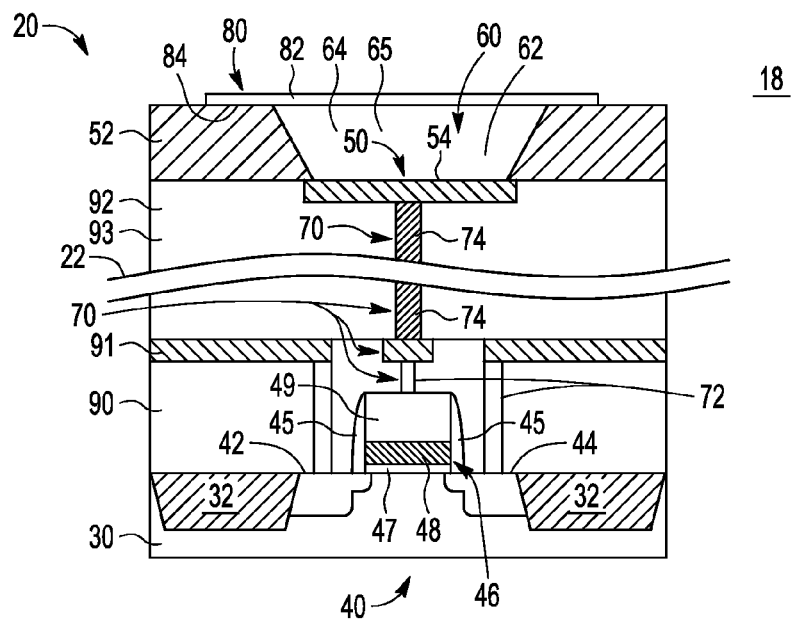
FIG. 1 is a schematic side view of a sensor field effect transistor.

Decreasing SFET electronic drift can be beneficial. In general, contact between the sense electrode and materials that are present within the ambient environment, such as when the materials adhere to the sense electrode or adsorb onto the sense electrode, can decrease an effective surface area of the sense electrode or can change an electrical characteristic of the sense electrode, both of which can contribute to the electronic drift. Closing, or covering, the analyte-receiving region, as disclosed herein, protects the sense electrode and decreases a potential for electronic drift of the SFET.

FIGS. 1-13 provide schematic examples of sensor field effect transistors (SFETs) 20. As illustrated, SFETs 20 are supported by a semiconductor substrate 30. As also illustrated, SFETs 20 include a field effect transistor 40. The field effect transistor includes a source 42, a drain 44, and a gate 46. As is known, or conventional, with field effect transistors, application of an electrical potential, or voltage, to gate 46 changes a resistance between source 42 and drain 44, thereby varying a magnitude of electric current flow between the source and the drain for a given voltage difference between the source and the drain.

As used herein, the phrase, "supported by," when referring to a relationship between semiconductor substrate 30 and one or more components of SFETs 20, is intended to indicate that SFETs 20 include both the semiconductor substrate, or a portion thereof, and the one or more components. It is within the scope of embodiments of the present invention that the one or more components of SFETs 20 can be "supported by" semiconductor substrate 30 in any suitable manner, including those that are conventional to semiconductor manufacturing technologies. As examples, the one or more components of SFETs 20 can be attached to the substrate, can be formed on the substrate, can be formed in the substrate, can be formed within the substrate, can be formed over the substrate, can be formed above the substrate, can extend from the substrate, can extend within the substrate, can extend above the substrate, or can extend over the substrate.

SFETs 20 further include at least one sense electrode 50. Sense electrode 50 is in electrical communication with gate 46 and is configured to apply an electrical potential, or voltage, to gate 46. A pre-use, or initial calibration, potential of a given SFET 20 can be controlled, or regulated, by varying a potential of gate 46. As an example, and during fabrication of the given SFET 20, a calibration device can be connected to the gate and can be utilized to move charges, or charged particles, onto or off of the gate to vary the potential of the gate.

As illustrated in FIGS. 1 and 3-13, sense electrode 50 can be separate, distinct, or spaced apart from gate 46. Under these conditions, SFETs 20 can include one or more electrical conduits 70 that can extend between, or electrically interconnect, sense electrode 50 and gate 46. Examples of electrical conduits 70 include any suitable contact, via, conductive trace, or metallization layer, or line.

FIGS. 1, 3-4, 6, and 8-13 illustrate a horizontal cut line 22 between field effect transistor 40 and sense electrode 50. This horizontal cut line is included to indicate that SFETs 20 can include any suitable number of electrical conduits 70, such as one or more metallization layers, between the field effect transistor and the sense electrode. This horizontal cut line also is included to indicate that SFETs 20 can include any suitable relative orientation, or geometry, between field effect transistor 40 and sense electrode 50. As an example, field effect transistor 40 can extend at least substantially below sense electrode 50, as illustrated in FIGS. 1-4, 6, and 8-13. As another example, field effect transistor 40 can be spaced apart from sense electrode 50 in a plane of semiconductor substrate 30, as illustrated in FIGS. 5 and 7. As yet another example, a longitudinal axis of sense electrode 50 can extend perpendicular to a longitudinal axis of gate 46. However, the longitudinal axis of sense electrode 50 also can be parallel to the longitudinal axis of gate 46.

As also illustrated in FIGS. 1-13, SFETs 20 include an analyte-receiving region 60 that is in fluid contact with sense electrode 50. Analyte-receiving region 60 is configured to receive an analyte fluid, and sense electrode 50 is configured such that fluid contact with the analyte fluid causes the sense electrode to develop an electrical potential, or voltage. This electrical potential, or voltage, can be generated by adsorption of one or more charged atoms, molecules, or particles from the analyte fluid onto the sense electrode, by reaction of one or more atoms, molecules, or particles from the analyte fluid with a surface of the sense electrode, by charge transfer between the analyte fluid and the sense electrode, or through formation of an electrical double layer within the analyte fluid and near the sense electrode.

Figure 2:
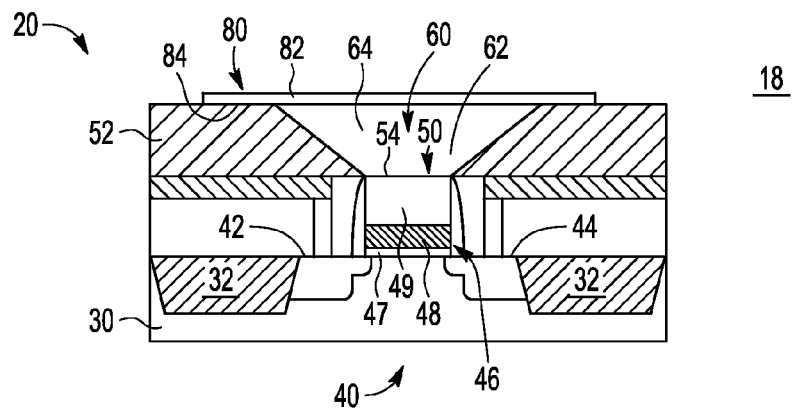
FIG. 2 is a schematic side view of a sensor field effect transistor.

During operation of SFETs 20, this electrical potential, or voltage, is applied to gate 46 either directly (as illustrated in FIG. 2) or via electrical conduit(s) 70 (as illustrated in FIGS. 1 and 3-13). This changes the resistance between source 42 and drain 44, as discussed. Thus, detection of the electric current flow between source 42 and drain 44 for a given voltage difference between the source and the drain can be utilized to quantify, determine, or detect one or more characteristics of the analyte fluid. As examples, SFETs 20 can detect a pH of the analyte fluid, an ionic strength of the analyte fluid, a concentration of one or more chemicals within the analyte fluid, or a concentration of one or more biological agents within the analyte fluid.

In each of these cases, a material from which the sense electrode is formed or a coating that covers the surface of the sense electrode can be selected to provide selective or non-selective interactions between one or more components of the analyte fluid and the sense electrode. These interactions change the electrical potential, or voltage, of the sense electrode, as described above. In the example of a pH-sensing SFET, the sense electrode can be formed such that the surface of the sense electrode includes hydroxyl groups that can be exposed to the analyte fluid. The hydroxyl groups can both donate a proton to the analyte fluid, thereby producing a negative charge on the surface of the substrate, and accept a proton from the analyte fluid, thereby producing a positive charge on the surface of the substrate. The ratio of positive to negative charges on the surface of the substrate varies with the proton concentration within the analyte fluid, thereby providing a mechanism for detection of the proton concentration within the analyte fluid.

Embodiments of the present invention provide at least a partial fluid isolation of analyte-receiving region 60 and sense electrode 50 from an ambient environment 18 that is proximal to, or surrounds, SFET 20. This at least partial fluid isolation decreases a potential for contact between sense electrode 50 and materials that can be present within the ambient environment, thereby decreasing electronic drift of SFET 20 or stabilizing a calibration of SFET 20. As examples, the at least partial fluid isolation of analyte-receiving region 60 can decrease a potential for contact between sense electrode 50 and particulate matter that is present within ambient environment 18, can decrease a potential for oxidation of sense electrode 50 by an oxidant that is present within the ambient environment, or can decrease a potential for adsorption of contaminants, such as hydrocarbons, onto sense electrode 50.

It is within the scope of embodiments of the present invention that the at least partial fluid isolation of analyte-receiving region 60 can be accomplished in any suitable manner. As an example, and as illustrated in FIGS. 1-13, analyte-receiving region 60 can be an enclosed analyte channel 62, at least prior to fluid contact between SFET 20 and the analyte fluid. As a more specific example, and as illustrated in FIGS. 1-4, 6, and 8-13, analyte-receiving region 60 can be formed within a void space 64 that is formed within an overlying layer 52 that extends above sense electrode 50. Examples of void space 64 include a trench or a depression that extends within overlying layer 52.

As illustrated in FIGS. 1-4, 6, and 10, a cover structure 80 can extend across void space 64, thereby at least partially enclosing the analyte-receiving region. Cover structure 80 can be a permanent, or fixed, cover structure, such as a glass cover structure, that remains in place during operation of SFET 20 or subsequent to contact between SFET 20 and the analyte fluid. Under these conditions, enclosed analyte channel 62 can extend between an analyte inlet 66 and an analyte outlet 68, as illustrated in FIGS. 5 and 7. Alternatively, cover structure 80 can be a temporary, or soluble, cover structure that is configured to dissolve, separate from, or otherwise be removed from SFET 20 subsequent to contact between SFET 20 and the analyte fluid. Under these conditions, cover structure 80 can be formed from a cover material 82 that is soluble within the analyte fluid, as illustrated in FIGS. 1-2. Additionally or alternatively, cover structure 80 can be attached to a remainder of SFET 20 with an attachment structure 84 that is soluble within the analyte fluid, as also illustrated in FIGS. 1-2.

As illustrated in FIG. 1, SFETs 20 further can include a plurality of additional structures that are known, or conventional to, field effect transistors or to metal oxide semiconductor (MOS) fabrication techniques and technologies. As an example, semiconductor substrate 30 can include a plurality of SFETs 20, and adjacent field effect transistors 40 of adjacent SFETs 20 can be electrically isolated from one another via trench isolation structures 32, which can extend within, or into, semiconductor substrate 30. As another example, electrical conduits 70 in the form of contacts 72 can extend within a first dielectric layer 90 and can electrically interconnect source 42, drain 44, and gate 46 with a plurality of additional electrical conduits 70 in the form of a first metallization layer 91. As yet another example, a gate dielectric 47 can extend between gate 46 and semiconductor substrate 30. As another example, gate 46 can include a polysilicon region 48 and a silicide region 49. As yet another example, spacers 45 can extend on either side of gate 46. As another example, one or more intermediate dielectric layer(s) 92, together with one or more corresponding intermediate metallization layers or vias 74, can extend between first metallization layer 91 and overlying layer 52. As another example, one or more devices for calibrating or reading the SFET can be supported by the semiconductor substrate. Such devices can be electrically connected to the gate utilizing electrical conduits 70.

First dielectric layer 90, intermediate dielectric layer(s) 92, and overlying layer 52 can include or be formed from any suitable material or materials. As examples, these layers can be formed from an electrically insulating material, such as silicon oxide. Similarly, electrical conduits 70, including contacts 72, vias 74, first metallization layer 91, or intermediate metallization layer(s) 93 can be formed from any suitable material or materials. As examples, these layers can be formed from a doped semiconducting material, a metallic material, aluminum, copper, or gold.

Semiconductor substrate 30 can be formed from any suitable semiconductor, or semiconducting, material or materials. As examples, semiconductor substrate 30 can be a silicon substrate, a gallium arsenide substrate, an epitaxial layer, a silicon on insulator substrate, or a semiconducting polymer substrate.

Similarly, sense electrode 50 can be formed from any suitable material or materials. As examples, sense electrode 50 can be a metallic sense electrode, an aluminum sense electrode, a copper sense electrode, or a gold sense electrode. With certain analyte fluids, sense electrode 50 can directly contact the analyte fluid. However, with other analyte fluids, SFET 20 further can include a surface coating 54 (as illustrated in FIGS. 1-2) that can be selected or configured to increase a sensitivity of SFET 20, to increase a magnitude of the electrical potential that is generated by contact between sense electrode 50 and the analyte fluid, or to decrease a potential for corrosion of sense electrode 50 by the analyte fluid.

As discussed, FIGS. 1-13 provide schematic examples of SFETs 20. FIGS. 1-13 are intended to illustrate various structures, functions, or features that can be included in or utilized with any SFET 20. As such, any structure, function, or feature that is disclosed herein with reference to any one of FIGS. 1-13 can be included in or utilized with any other of FIGS. 1-13 without departing from the scope of the present disclosure.

Turning specifically to FIG. 1, an SFET 20 in which sense electrode 50 is spaced apart from gate 46 is illustrated. Such an SFET is also illustrated in FIGS. 3-13. Therein, one or more electrode conductors, in the form of electrical conduits 70, electrically interconnects (or provides electrical communication between) gate 46 and sense electrode 50. As illustrated in FIG. 1, analyte-receiving region 60 includes a trench 65 that extends within overlying layer 52 and that is bounded by sense electrode 50, overlying layer 52, and cover structure 80. Cover structure 80 can extend across any suitable portion of trench 65, thereby enclosing the trench or forming enclosed analyte channel 62. As an example, cover structure 80 can extend across at least a portion of trench 65 that is opposed to sense electrode 50. In the examples of FIG. 1, and also in FIGS. 2-5 and 10, analyte-receiving region 60 includes a single enclosed analyte channel 62. In the embodiments of FIGS. 1-4, 6, and 10, cover structure 80 can be operatively attached, or adhered, to overlying layer 52 after removal of a portion of the overlying layer to form void space 64.

FIG. 2 illustrates an SFET 20 in which sense electrode 50 is proximal to, is not spaced apart from, or forms a portion of gate 46. As such, SFET 20 of FIG. 2 does not include electrical conductors that extend between the sense electrode and the gate. Under these conditions, surface coating 54 can extend across gate 46. However, this is not required. The SFET of FIG. 2 can be fabricated utilizing fewer process steps than the SFET of FIG. 1; however, electronic drift can be more significant with this configuration due to the potential for more direct contact between gate 46 and ambient environment 18.

Figure 3:
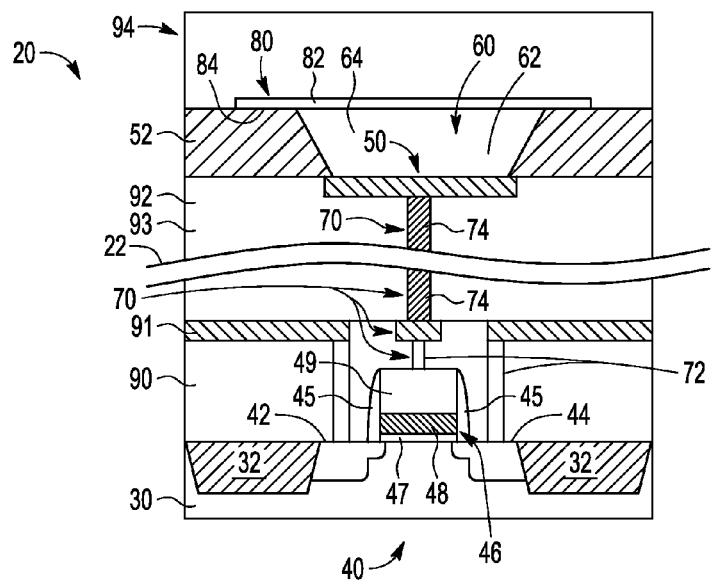
FIG. 3 is a schematic side view of a sensor field effect transistor.

FIG. 3, and additionally FIGS. 4, 6, and 8-13, illustrates that one or more upper dielectric layers 94 can extend above, or form, cover structure 80. These upper dielectric layers can contain, seal, passivate, or otherwise protect a separate cover structure 80 or analyte-receiving region 60, as illustrated in FIGS. 3-4, 6, and 10. Additionally or alternatively, these upper dielectric layers also can contain, seal, passivate, protect, or provide support for one or more upper metallization layers 95, as illustrated in FIGS. 4, 6, 8-9, and 11-13. The upper dielectric layers 94 also can form, or define, cover structure 80, as illustrated in FIGS. 8-9 and 11-13 and discussed in more detail herein. Upper dielectric layers 94 can be patterned to provide one or more analyte inlets and analyte outlets that permit the analyte fluid to enter analyte-receiving region 60, as also discussed in more detail herein.

Figure 4:
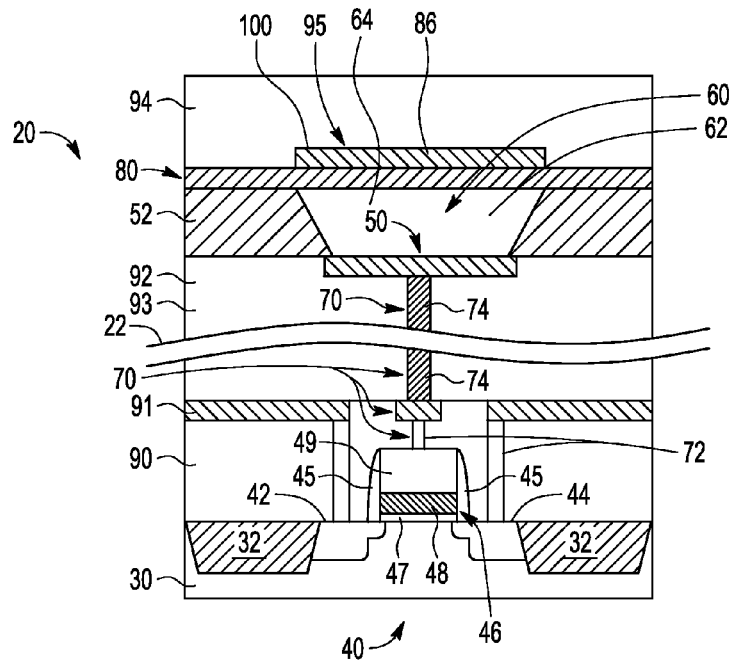
FIG. 4 is a schematic side view of a sensor field effect transistor.
Figure 5:
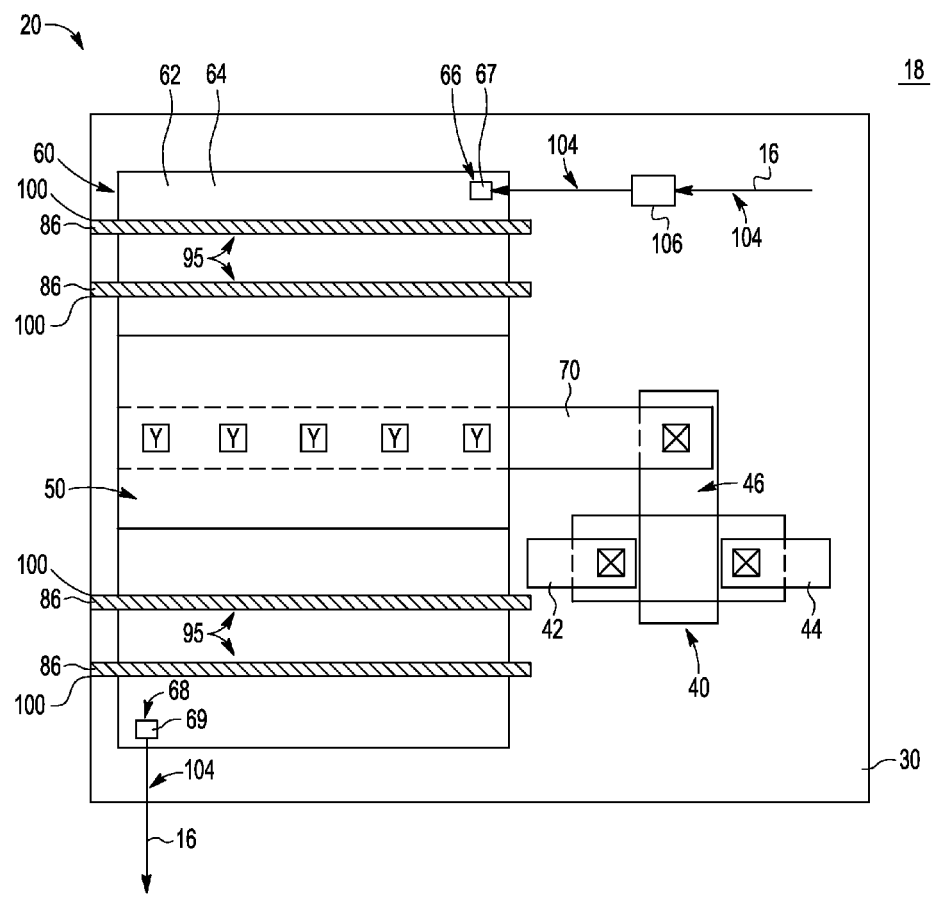
FIG. 5 is a schematic top view of a sensor field effect transistor.

FIG. 4, and additionally FIGS. 6, 8-9, and 11-13, illustrates that upper metallization layer 95 can extend over, or above, cover structure 80 or within upper dielectric layer 94. In FIG. 4, upper metallization layer 95 forms a portion of a microfluidic drive structure 100 that is configured to provide a motive force for flow of the analyte fluid through enclosed analyte channel 62. As an example, microfluidic drive structure 100 can be an electroosmotic drive structure that is configured to generate an electric field that provides the motive force for flow of the analyte fluid. Thus, SFETs 20 that include microfluidic drive structures 100 can be configured to pump the analyte fluid through the enclosed analyte channel without the need for, or without utilizing, an external fluid pressure source, such as an external pump. A plurality of electrical lines 86 can be formed from upper metallization layer 95, and can extend across enclosed analyte channel 62, extend perpendicular to enclosed analyte channel 62, or extend at least substantially perpendicular to enclosed analyte channel 62. Because electrical lines 86 extend perpendicular to enclosed analyte channel 62, the electrical lines can be utilized to generate the electric field and provide the motive force for flow of the analyte fluid without the need to provide a ground point between electrical lines 86 and sense electrode 50. However, electrical lines that extend parallel to the enclosed analyte channel are also within the scope of embodiments of the present invention.

FIG. 5 is a schematic top view of an SFET 20. The SFET of FIG. 5 includes a single analyte-receiving region 60 that extends in contact with a single sense electrode 50. The SFET further includes an analyte inlet 66, which is configured to receive an analyte fluid 16 into analyte-receiving region 60 and an analyte outlet 68, which is configured to permit the analyte fluid to exit, or to be discharged from, the analyte-receiving region. As illustrated, analyte inlet 66 and analyte outlet 68 are spaced apart from one another and also can be spaced apart from the sense electrode. This can include being spaced apart along a length of the analyte-receiving region or of the enclosed analyte channel. Such a configuration can provide for flow of the analyte fluid across the sense electrode while, at the same time, decreasing a potential for electronic drift of the sense electrode due to contamination via contact with the ambient environment that surrounds the SFET. As also illustrated, SFET 20 can include one or more fluid conduits 104 that can be configured to convey the analyte fluid to the analyte inlet or to receive the analyte fluid from the analyte outlet.

As used herein, the phrase, "extends in contact with," when referring to the relationship between the analyte-receiving region and the sense electrode, is intended to indicate that the analyte-receiving region is at least partially defined, or bounded, by the sense electrode. As such, an analyte fluid that is present, or flows, within the analyte-receiving region also will be in fluid contact with the sense electrode, thereby permitting the SFET to measure, or monitor, one or more properties of the analyte fluid via the sense electrode. With this in mind, the phrase, "extends in contact with" also can be referred to herein as extending in fluid contact with, extending in fluid communication with, or simply as being in fluid communication. Additionally or alternatively, the analyte-receiving region also can be referred to herein as being configured to permit fluid contact between the analyte fluid and the sense electrode or as being configured to direct the analyte fluid past, or into fluid contact with, the sense electrode.

It is within the scope of embodiments of the present disclosure that SFET 20 further can include a soluble inlet cover structure 67 or a soluble outlet cover structure 69. Soluble inlet cover structure 67, when present, extends across analyte inlet 66 and is formed from a cover material that is soluble within the analyte fluid. Similarly, soluble outlet cover structure 69, when present, extends across analyte outlet 68 and is formed from the soluble cover material. As such, and prior to fluid contact between SFET 20 and the analyte fluid, soluble inlet cover 67 or soluble outlet cover 69 fluidly isolates analyte-receiving region 60 from the ambient environment. However, subsequent to fluid contact between SFET 20 and the analyte fluid, soluble inlet cover 67 and soluble outlet cover 69, when present, dissolve within the analyte fluid, thereby permitting flow of analyte fluid 16 into analyte inlet 66, through analyte-receiving region 60, or out of analyte outlet 68.

It is also within the scope of embodiments of the present disclosure that SFET 20 further can include a microfluidic separation structure 106. Microfluidic separation structure 106 can be configured to separate at least one component of analyte fluid 16 from at least one other component of analyte fluid 16 prior to contact between the analyte fluid and sense electrode 50. Thus, SFET 20 can be configured such that a first portion of the analyte fluid contacts sense electrode 50, while a second portion of the analyte fluid does not contact sense electrode 50. Such a configuration can increase a sensitivity of SFET 20 to a specific, or targeted, component of analyte fluid 16, such as can be contained within the first portion of the analyte fluid, or can decrease a potential for contamination of the sense electrode, such as by the at least one component of the analyte fluid that is separated in the second portion of the analyte stream.

An example of microfluidic separation structure 106 includes a mechanical separation structure, such as a filter or a membrane, that physically limits or restricts flow of one or more components of analyte fluid 16 while permitting flow of one or more other components of analyte fluid 16. Additionally or alternatively, microfluidic separation structure 106 can be an electrically driven separation structure. As an example, microfluidic separation structure 106 can apply an electrostatic field to analyte fluid 16, and this electrostatic field can be utilized to separate charged components of the analyte fluid from neutral components of the analyte fluid or to separate oppositely charged components of the analyte fluid. As another example, the microfluidic separation structure can apply an alternating electric field to the analyte fluid, and this alternating field can selectively accelerate certain sized components of analyte fluid 16 or components of analyte fluid 16 that have a preselected mass to charge ratio. The electrically driven separation structure can be a separate or distinct structure, as illustrated. Alternatively, the electrically driven separation structure can apply the electric field to the analyte fluid via microfluidic drive structure 100. As additional examples, microfluidic separation structure 106 can include one or more of an ionic charge-based separation structure, a polarity-based separation structure, or a mass-based separation structure that is configured to separate the at least one component from the at least one other component based upon a size, an ionic charge, a polarity, or a mass difference, respectively, between the at least one component and the at least one other component FIGS. 5 and 7 also illustrate a microfluidic drive structure 100 in the form of an electroosmotic drive structure that includes a plurality of electrical lines 86. Electrical lines 86 can extend perpendicular to a length of enclosed analyte channel 62, as discussed.

Figure 6:
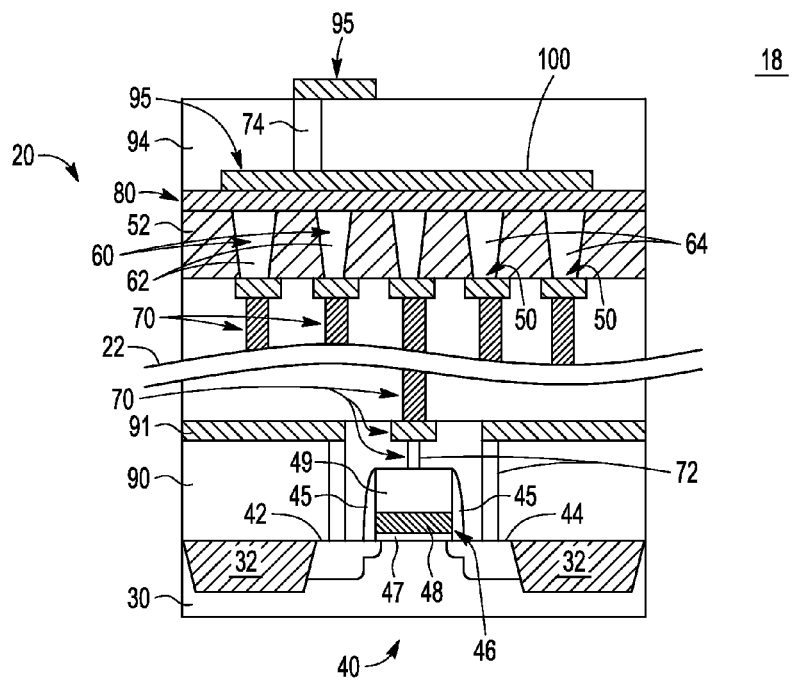
FIG. 6 is a schematic side view of a sensor field effect transistor.
Figure 7:
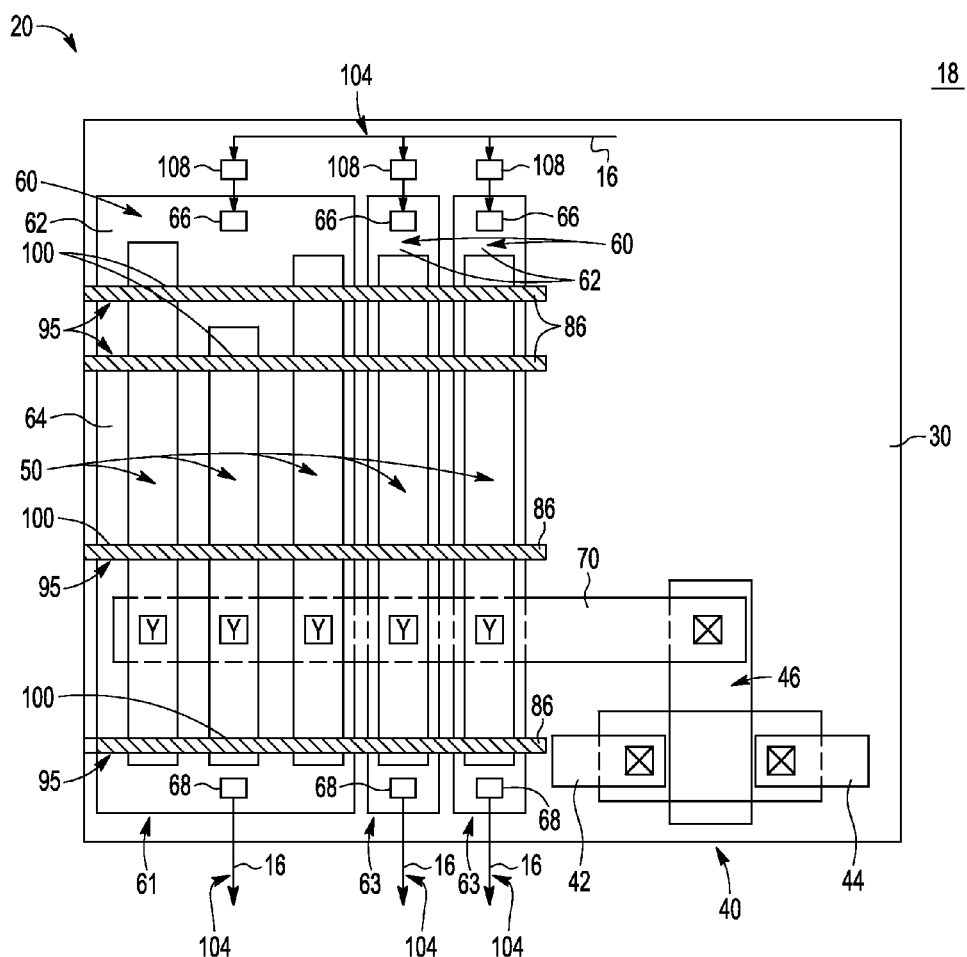
FIG. 7 is a schematic top view of a sensor field effect transistor.

As illustrated in FIG. 6, and additionally in FIGS. 7-9 and 11-13, SFET 20 can include a plurality of separate, distinct, or spaced apart analyte-receiving regions 60, such as a plurality of separate, distinct, or spaced apart enclosed analyte channels 62. In the embodiments of FIGS. 6-7, 9, and 12-13 at least one of the plurality of spaced apart analyte-receiving regions is associated with a corresponding, or respective, sense electrode 50 of a plurality of sense electrodes 50. Each sense electrode 50 is in electrical communication with gate 46 of field effect transistor 40. FIG. 6 further illustrates that one or more upper metallization layers 95, which can form a portion of microfluidic drive structure 100, can be electrically connected with an upper surface of SFET 20, such as through a via 74. Additionally or alternatively, the SFET 20 can include an on-chip drive circuit that is configured to electrically drive the microfluidic drive structure. Such a configuration can permit electrical biasing of microfluidic drive structure 100, thereby permitting generation of an electric field within analyte-receiving region 60, with this electric field providing a motive force for flow of the analyte fluid through the analyte-receiving region, as discussed in more detail herein.

When SFET 20 includes the plurality of spaced apart enclosed analyte channels 62, the SFET can be configured such that the analyte fluid is simultaneously provided to each, or every, analyte channel 62. Such a configuration can improve control of or increase a flow rate of the analyte fluid within the enclosed analyte channels due to an increased surface area for contact between the analyte fluid and the SFET.

Alternatively, the SFET also can be configured such that the analyte fluid is selectively allowed to flow through at least one enclosed analyte channel that is associated with the SFET without being allowed to flow through at least one other enclosed analyte channel that is associated with the SFET. Under these conditions, SFET 20 further can include a selection structure 108, as illustrated in FIG. 7, that is configured to permit selective control of the flow of the analyte fluid through one or more of the enclosed analyte channels. Such a configuration can permit a single SFET 20 to be utilized to test a plurality of different analyte fluids or can permit a user to selectively utilize a first sense electrode for a first period of time and subsequently to utilize a second sense electrode for a second period of time. As an example, the user can utilize the first sense electrode until the first sense electrode becomes ineffective or contaminated and then can transition to utilizing the second sense electrode. Examples of selection structure 108 include any suitable flow restriction, valve, or electric field.

FIG. 7 is a schematic top view of an SFET 20. The SFET of FIG. 7 includes a plurality of analyte-receiving regions 60, such as a plurality of enclosed analyte channels 62. In the example of FIG. 7, a first analyte-receiving region 60, which is indicated at 61, extends in contact with a plurality of (e.g., 3) sense electrodes 50, while second and third analyte-receiving regions 60, which are indicated at 63, extend in contact with respective single sense electrodes 50. These are simply examples, and it is within the scope of embodiments of the present invention that a given analyte-receiving region 60 can be associated with any suitable number of sense electrodes 50. When SFET 20 includes the plurality of spaced-apart enclosed analyte channels, each of the analyte channels can extend between a respective analyte inlet 66 and a respective analyte outlet 68, as illustrated.

Figure 8:
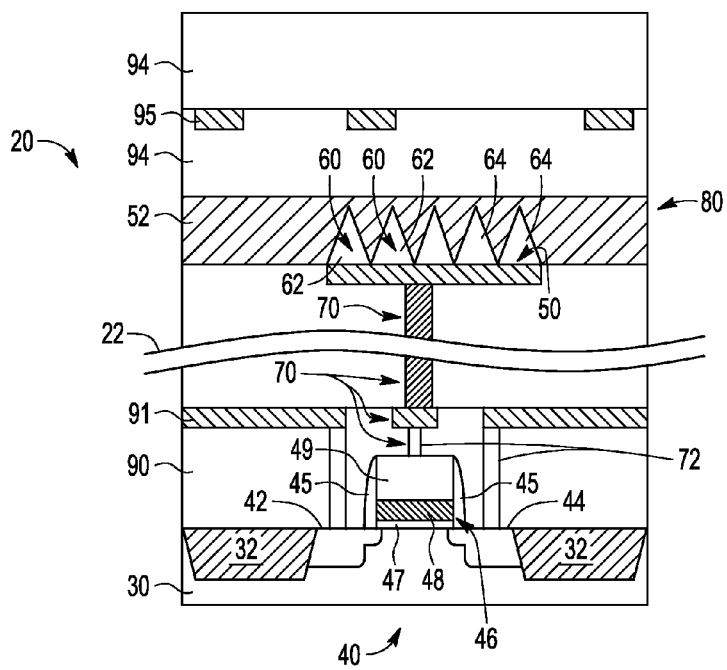
FIG. 8 is a schematic side view of a sensor field effect transistor.

FIG. 8 is a schematic side view of an SFET 20 that includes a single sense electrode 50 and a plurality of spaced apart enclosed analyte channels 62 that extends in contact with the single sense electrode. In the embodiment of FIG. 8, and also of FIGS. 9 and 11-13, enclosed analyte channels 62 can have a quasi-triangular, or keyhole, cross-sectional shape, as illustrated. Such a cross-sectional shape can be obtained by forming a plurality of spaced apart void spaces 64 within a portion of overlying layer 52 and subsequently performing a non-conformal deposition process to deposit additional dielectric material, such as upper dielectric layer 94, above the portion of overlying layer 52. Such a non-conformal deposition process generally will fill an upper opening of the plurality of spaced-apart void spaces prior to filling a lower region of the plurality of spaced-apart void spaces, thereby enclosing the upper opening and forming the plurality of spaced apart enclosed analyte channels. In contrast with the embodiments of FIGS. 1-4, 6, and 10, which include a separate cover structure 80, the enclosed analyte channels of FIGS. 8-9 and 11-13 can be formed utilizing known, or conventional, semiconductor processing techniques (i.e., the non-conformal deposition process) to define cover structure 80 with upper dielectric layer 94. This can decrease a cost associated with fabrication of SFETs 20 that include the enclosed analyte channels that are illustrated in FIGS. 8-9 and 11-13 when compared to the SFETs 20 that include the enclosed analyte channels of FIGS. 1-4, 6, and 10.

Figure 9:
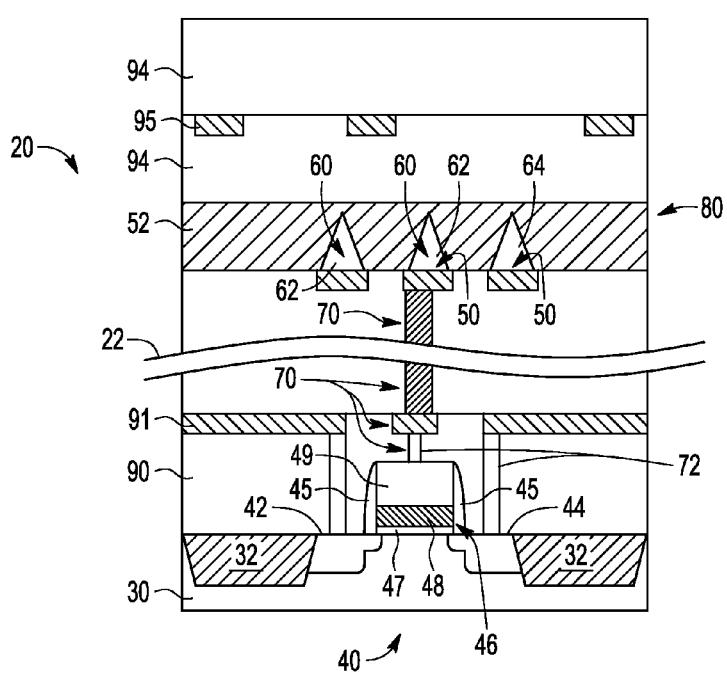
FIG. 9 is a schematic side view of a sensor field effect transistor.

FIG. 9 illustrates an alternative embodiment of SFET 20 that includes a plurality of spaced apart analyte-receiving regions 60, in the form of a plurality of spaced apart enclosed analyte channels 62, that are formed via the above-described non-conformal deposition process. In FIG. 9, each of the enclosed analyte channels is associated with a corresponding sense electrode 50. The sense electrodes all are in electrical communication with gate 46. As discussed, such a configuration can permit selective or independent control of the flow of the analyte fluid through the analyte-receiving regions.

Figure 10:
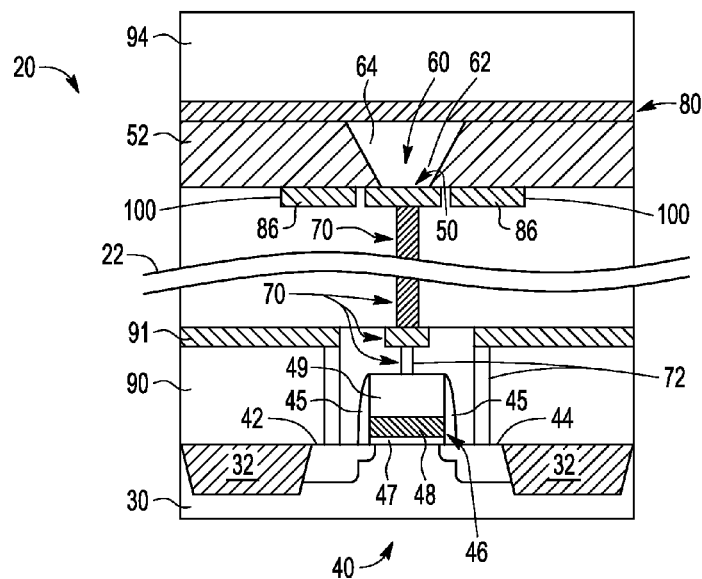
FIG. 10 is a schematic side view of a sensor field effect transistor.

FIG. 10 illustrates an alternative embodiment of SFET 20 that includes a microfluidic drive structure 100 in the form of an electroosmotic drive structure that includes a pair of electrical lines 86. Electrical lines 86 can be coplanar, or at least substantially coplanar, with sense electrode 50. Additionally or alternatively, electrical lines 86 can be formed at least substantially concurrently with sense electrode 50. As discussed, electrical lines 86 can be electrically biased to generate an electric field, and this electric field can control, regulate, or provide a motive force for flow of the analyte fluid through enclosed analyte channel 62.

Figure 11:
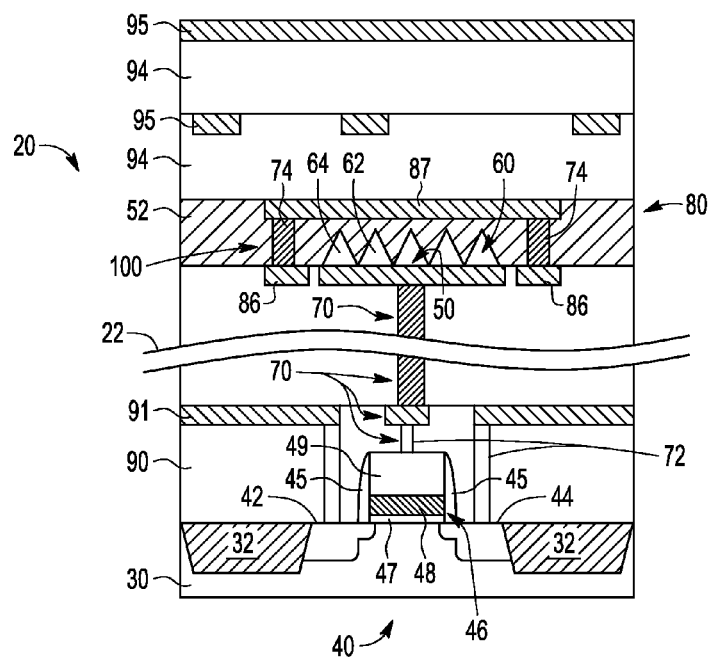
FIG. 11 is a schematic side view of a sensor field effect transistor.

FIG. 11 illustrates another alternative embodiment of SFET 20 that includes a microfluidic drive structure 100 in the form of an electroosmotic drive structure. In FIG. 11, the electroosmotic drive structure includes a pair of electrical lines 86 that is at least substantially coplanar with sense electrode 50, another electrical line 87 that extends above enclosed analyte channels 62, and a pair of vias 74 that electrically interconnect the pair of electrical lines that is coplanar with the sense electrode and the electrical line that extends above the enclosed analyte channels. Thus, and in the embodiment of FIG. 11, microfluidic drive structure 100 surrounds three sides of enclosed analyte channels 62. Such a configuration can increase a magnitude of the electric field applied to enclosed analyte channels 62 by the microfluidic drive structure, thereby increasing a flow rate, or a control of the flow rate, of the analyte fluid within the enclosed analyte channels.

Figure 12:
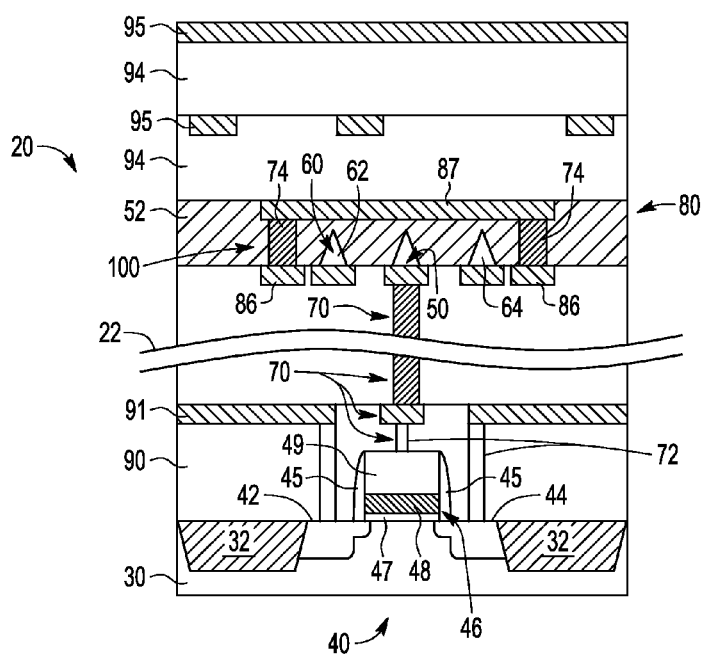
FIG. 12 is a schematic side view of a sensor field effect transistor.

FIG. 12 illustrates yet another alternative embodiment of SFET 20. The SFET of FIG. 12 includes a microfluidic drive structure 100 that is at least substantially similar to the microfluidic drive structure of FIG. 11. However, and similar to FIG. 9, the SFET of FIG. 12 includes a plurality of spaced apart analyte-receiving regions 60 and a corresponding plurality of spaced apart sense electrodes 50. Such a configuration can provide increased control over the flow, or flow rate, of the analyte fluid that flows within analyte-receiving regions 60, as discussed herein with reference to FIG. 11. In addition, the configuration of FIG. 12 also can be utilized to provide selective, or independent, control of the flow of the analyte fluid through the analyte-receiving regions, as discussed herein with reference to FIG. 9.

Figure 13:
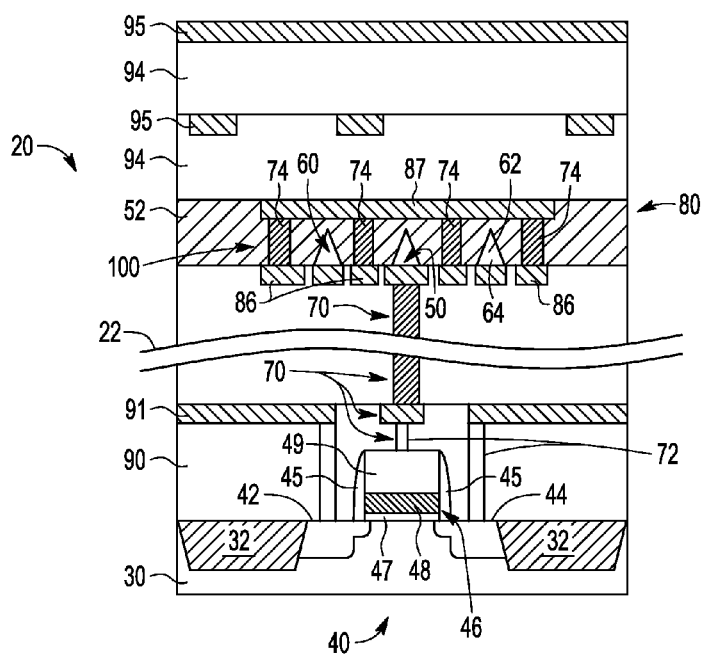
FIG. 13 is a schematic side view of a sensor field effect transistor.

FIG. 13 illustrates another alternative embodiment of SFET 20. The SFET of FIG. 13 includes a plurality of analyte-receiving regions 60 and a corresponding plurality of sense electrodes 50. In addition, the SFET of FIG. 13 also includes a microfluidic drive structure 100 that surrounds each analyte-receiving region on three sides. Such a configuration can provide an even higher magnitude of the electric field applied to the analyte fluid when the analyte fluid flows within the analyte-receiving regions or can provide even greater control over the flow, or flow rate, of the analyte fluid.

Figure 14:
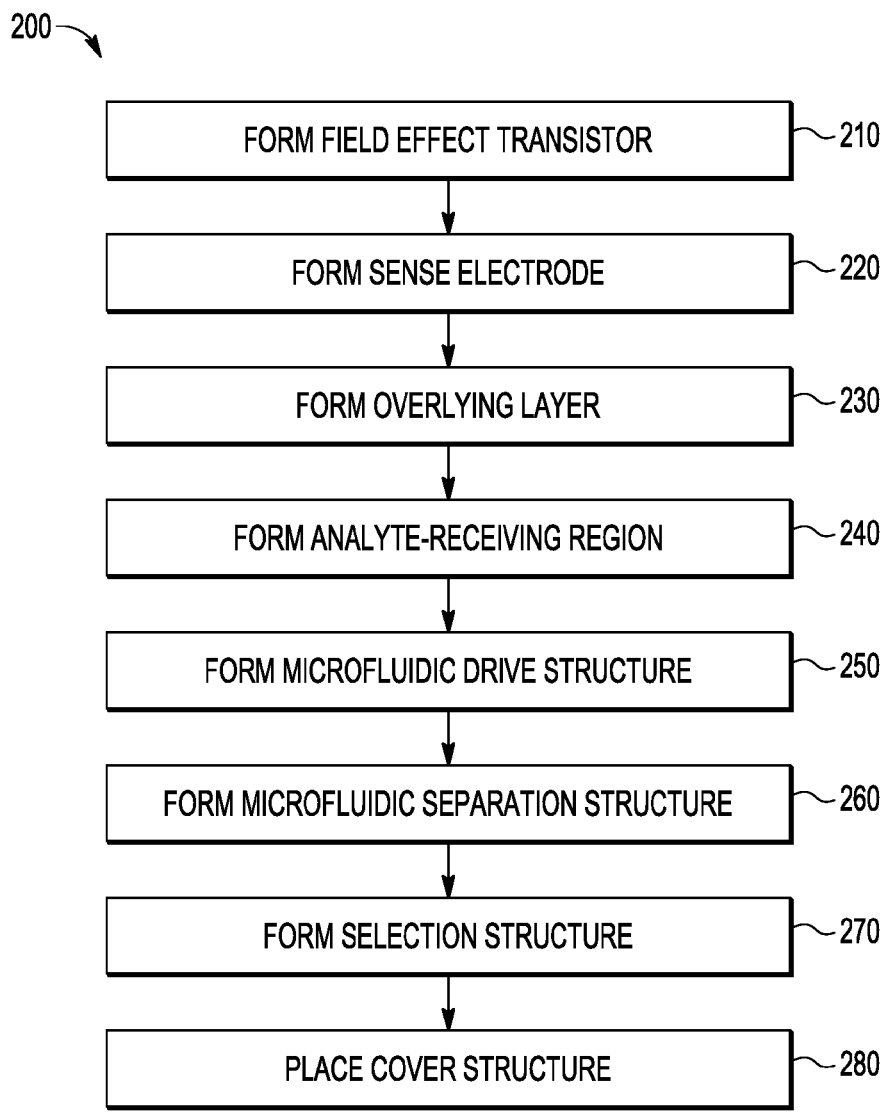
FIG. 14 is a flowchart depicting methods of fabricating a sensor field effect transistor.

FIG. 14 is a flowchart depicting methods 200 of fabricating a sensor field effect transistor (SFET), while FIGS. 15-23 illustrate a process flow that can be utilized to form a sensor field effect transistor (SFET) 20 or that can illustrate methods 200. Methods 200 can include forming a field effect transistor at 210, forming a sense electrode at 220, forming an overlying layer at 230, or forming an analyte-receiving region at 240. Methods 200 further can include forming a microfluidic drive structure at 250, forming a microfluidic separation structure at 260, forming a selection structure at 270, or placing a cover structure at 280.

Forming the field effect transistor at 210 can include forming the field effect transistor on, over, or within, a semiconductor substrate. This can include forming the field effect transistor such that the field effect transistor is at least partially defined by the substrate, forming the field effect transistor such that the field effect transistor is supported by the substrate, or forming the field effect transistor such that the field effect transistor extends at least partially above a surface of the substrate. The field effect transistor can include a source, a drain, and a gate; and the forming at 210 can include forming the source, forming the drain, and forming the gate in any suitable sequence or utilizing any suitable process, or processes, including those that are known, or conventional to, metal oxide semiconductor field effect transistor processing technologies. As examples, the forming at 210 can include performing one or more of a deposition process, a sputter process, a crystal growth process, a diffusion process, an implant process, an annealing process, a polish process, a lithography process, a damascene process, a wet etch process, and a dry etch process.

Figure 15:
FIG. 15 is a schematic side view of a portion of a process flow for fabrication of a sensor field effect transistor.
Figure 16:
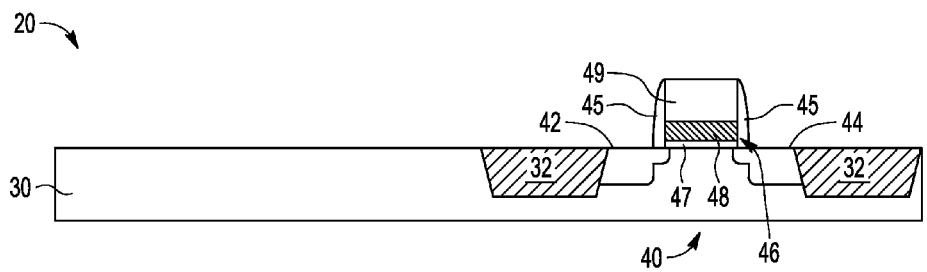
FIG. 16 is a schematic side view of a portion of a process flow for fabrication of a sensor field effect transistor.

The forming at 210 is illustrated in FIGS. 15-16. As illustrated in FIG. 15, and prior to the forming at 210, a semiconductor substrate 30 does not have the field effect transistor formed thereon. As illustrated in FIG. 16, and subsequent to the forming at 210, a field effect transistor 40 can be at least partially supported by semiconductor substrate 30. The various components or structures of field effect transistor 40 are conventional to field effect transistors and are discussed herein.

The forming at 210 further can include calibrating the SFET, such as by setting, specifying, or defining a pre-use, or initial calibration, potential of the SFET. As an example, a calibration device can be connected to the gate and can be utilized to move charges, or charged particles, onto or off of the gate to vary the potential of the gate. The calibrating can be performed at any suitable time or with any suitable sequence within methods 200. As an example, the calibrating can be performed subsequent to forming at least the gate of the SFET, subsequent to the forming at 220, subsequent to the forming at 230, subsequent to the forming at 240, subsequent to the forming at 250, subsequent to the forming at 260, subsequent to the forming at 270, or subsequent to the placing at 280.

Figure 17:
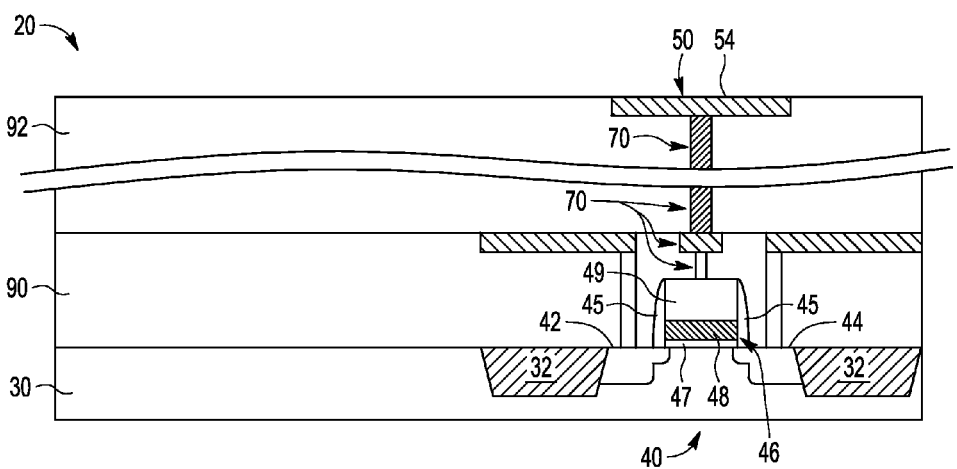
FIG. 17 is a schematic side view of a portion of a process flow for fabrication of a sensor field effect transistor.

Forming the sense electrode at 220 can include forming the sense electrode on, above, or within the semiconductor substrate and is illustrated in FIG. 17. As illustrated, the forming at 220 can include forming a sense electrode 50 such that the sense electrode is in electrical communication with, or is electrically connected to, a gate 46 of field effect transistor 40. As also illustrated, the sense electrode can be separate, or spaced apart, from the gate. Under these conditions, the forming at 220 can include forming the sense electrode subsequent to the forming at 210, subsequent to forming the gate, subsequent to forming an intermediate dielectric layer 92, or subsequent to forming a plurality of electrical conduits 70 that electrically interconnects the sense electrode and the gate. As discussed herein, and illustrated in FIG. 2, the sense electrode alternatively can form a portion of the gate. Under these conditions, the forming at 220 can include forming the sense electrode at least partially concurrently with the forming at 210 or with the forming the gate of the field effect transistor.

The forming at 220 can be performed in any suitable manner or utilizing any suitable process or processes. As examples, the forming at 220 can include performing one or more of a deposition process, a sputter process, a polish process, a lithography process, a damascene process, a dry etch process, and a wet etch process.

The forming at 220 further can include forming a surface coating, such as surface coating 54 of FIG. 17, on the sense electrode. As discussed, the surface coating can, or can be utilized to, provide additional, specific, or desired sensitivity of the sense electrode to certain chemicals, compounds, compositions, or materials. The surface coating can be formed in any suitable manner, including those that are known, or conventional, to semiconductor fabrication or are discussed herein. In addition, the surface coating can be formed at any suitable time or with any suitable sequence during methods 200. As examples, the surface coating can be formed concurrently with formation of the sense electrode at 220, subsequent to formation of the sense electrode at 220, during the forming at 240, or subsequent to the forming at 240.

Figure 19:
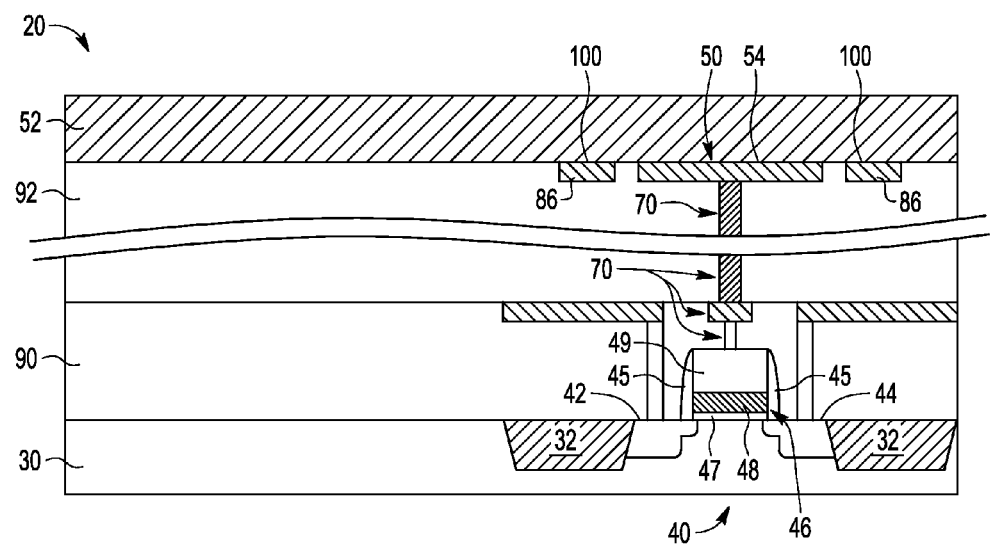
FIG. 19 is a schematic side view of a portion of a process flow for fabrication of a sensor field effect transistor.

Forming the overlying layer at 230 can include forming the overlying layer on the semiconductor substrate and is illustrated in FIG. 19 at 52. The forming at 230 also can include forming the overlying layer such that the overlying layer extends across a surface of the semiconductor substrate, extends across the sense electrode, covers the sense electrode, or extends in contact with the sense electrode, as illustrated. The forming at 230 can be performed in any suitable manner or utilizing any suitable process or processes. As examples, the forming at 230 can include performing one or more of a deposition process, a diffusion process, a lithography process, a dry etch process, and a wet etch process.

Figure 20:
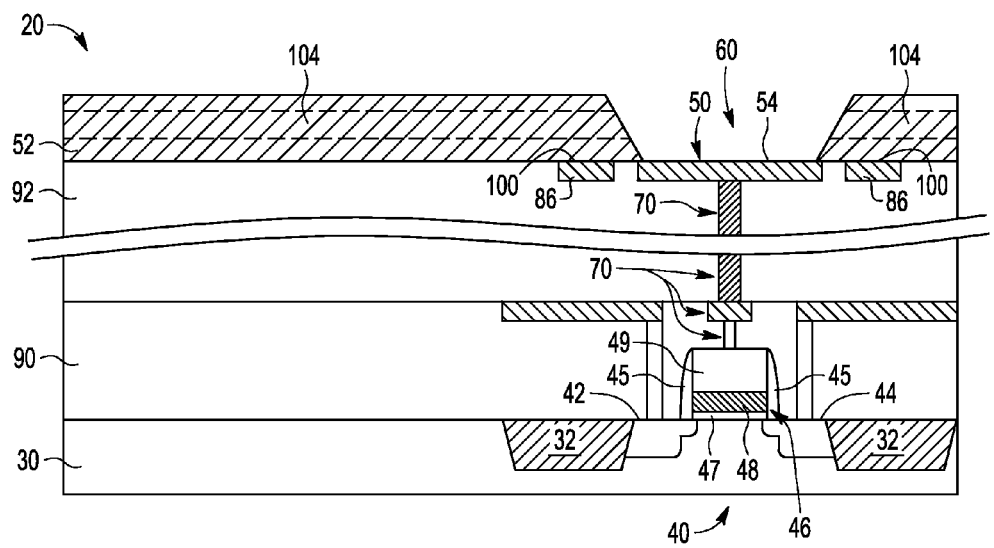
FIG. 20 is a schematic side view of a portion of a process flow for fabrication of a sensor field effect transistor.

Forming the analyte-receiving region at 240 can include forming the analyte-receiving region within the overlying layer, forming such that the analyte-receiving region extends in contact with the sense electrode, or forming such that the analyte-receiving region extends above the sense electrode and is illustrated in FIG. 20 at 60. As examples, the forming at 240 can include removing a portion of the overlying layer that extends in contact with the sense electrode, forming a void space within the overlying layer, forming a depression within the overlying layer, or forming a trench within the overlying layer.

As also illustrated in FIG. 20, the forming at 240 further can include forming one or more fluid conduits 104 within overlying layer 52 or in another layer that can extend above or below overlying layer 52. Fluid conduits 104 can fluidly interconnect analyte-receiving region 60 with one or more other components, regions, or portions of SFET 20, as discussed in more detail herein. Fluid conduits 104 are illustrated in dashed lines in FIG. 20 to indicate that the fluid conduits are not necessarily intersected by the cross-section of FIG. 20 or to indicate that the fluid conduits can have any suitable shape, depth, or configuration.

The forming at 240 can be performed in any suitable manner or utilizing any suitable process or processes. As examples, the forming at 240 can include performing one or more of a lithography process, a dry etch process, and a wet etch process.

Figure 18:
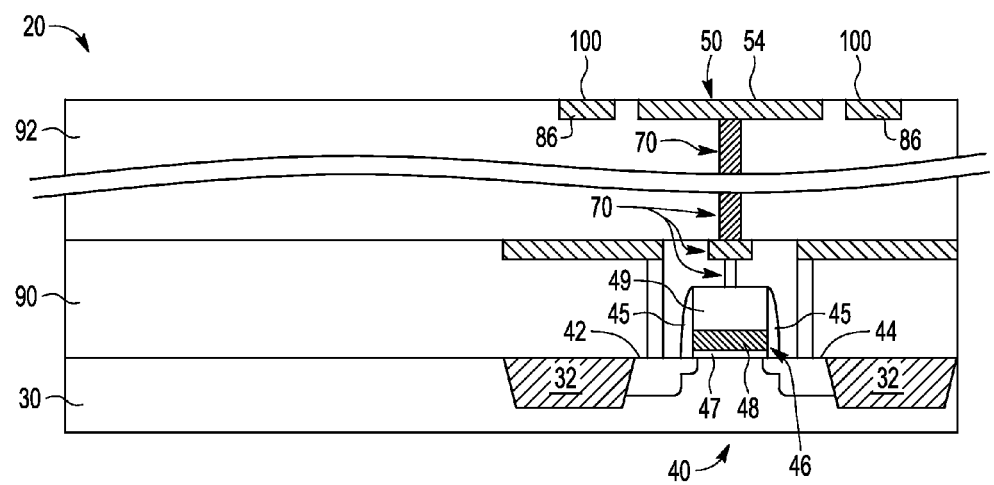
FIG. 18 is a schematic side view of a portion of a process flow for fabrication of a sensor field effect transistor.

Forming the microfluidic drive structure at 250 can include forming any suitable microfluidic drive structure on, or in, the semiconductor substrate in any suitable manner and is illustrated in FIG. 18 at 100. As an example, the SFET can be configured to convey an analyte fluid within an enclosed analyte channel that includes the analyte-receiving region and that extends between an analyte inlet and an analyte outlet. Under these conditions, the microfluidic drive structure can be configured to provide a motive force for flow of the analyte fluid within the enclosed analyte channel or between the analyte inlet and the analyte outlet. The microfluidic drive structure can include any suitable structure that can provide the motive force for flow of the analyte fluid. As examples, the microfluidic drive structure can include an electroosmotic drive structure, which includes a plurality of electrical lines 86 that is supported by the semiconductor substrate, or a peristaltic drive structure, which includes a peristaltic pump that is supported by the semiconductor substrate. The forming at 250 can be performed in any suitable manner or utilizing any suitable process or processes. As examples, the forming at 250 can include performing one or more of a deposition process, a sputter process, a polish process, a lithography process, a damascene process, a wet etch process, and a dry etch process.

In the example of FIG. 18, microfluidic drive structure 100 is illustrated as being formed within intermediate dielectric layer 92. Under these conditions, microfluidic drive structure 100 can be referred to herein as being coplanar, or at least substantially coplanar, with sense electrode 50 and the forming at 250 can be performed concurrently, or at lease substantially concurrently, with the forming at 220. However, this configuration is not required, and at least a portion of the microfluidic drive structure can be formed subsequent to the forming at 220, as illustrated in the embodiments of FIGS. 4-7 and 10-13.

Figure 21:
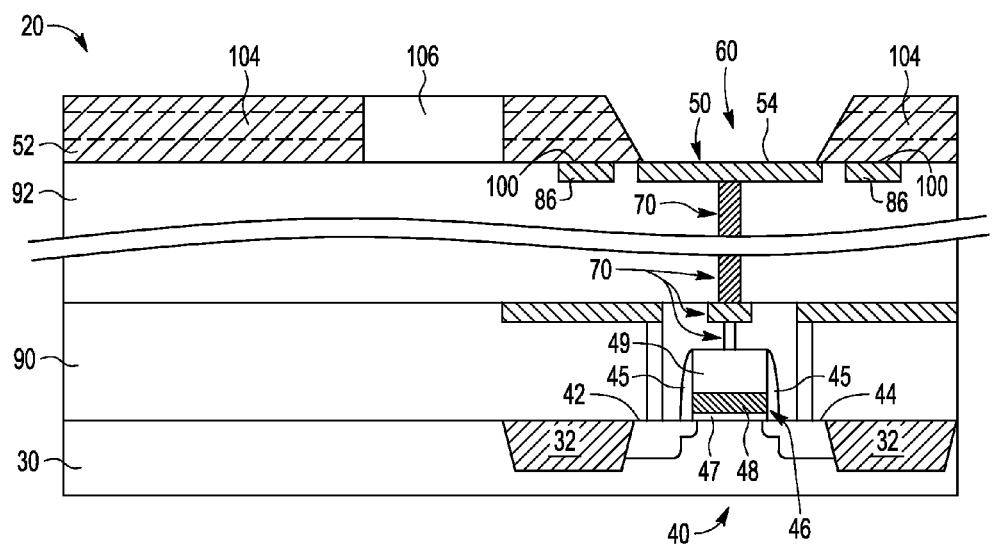
FIG. 21 is a schematic side view of a portion of a process flow for fabrication of a sensor field effect transistor.

Forming the microfluidic separation structure at 260 can include forming any suitable microfluidic structure on, or in, the semiconductor substrate in any suitable manner and is illustrated in FIG. 21 at 106. As an example, SFET 20 can be configured to convey the analyte fluid within the enclosed analyte channel and between the analyte inlet and the analyte outlet. Under these conditions, microfluidic separation structure 106 can be configured to separate at least one component of the analyte fluid from at least one other component of the analyte fluid when, or while, the analyte fluid flows through the enclosed analyte channel, when, or while, the analyte fluid flows to the enclosed analyte channel within fluid conduit 104, or prior to contact between the analyte fluid and sense electrode 50.

The microfluidic separation structure can include any suitable structure that can separate the at least one component from the at least one other component, examples of which are disclosed herein. The forming at 260 can be performed in any suitable manner or utilizing any suitable process or processes. As examples, the forming at 260 can include performing one or more of a deposition process, a sputter process, a diffusion process, an implant process, an annealing process, a polish process, a lithography process, a damascene process, a wet etch process, and a dry etch process.

Figure 22:
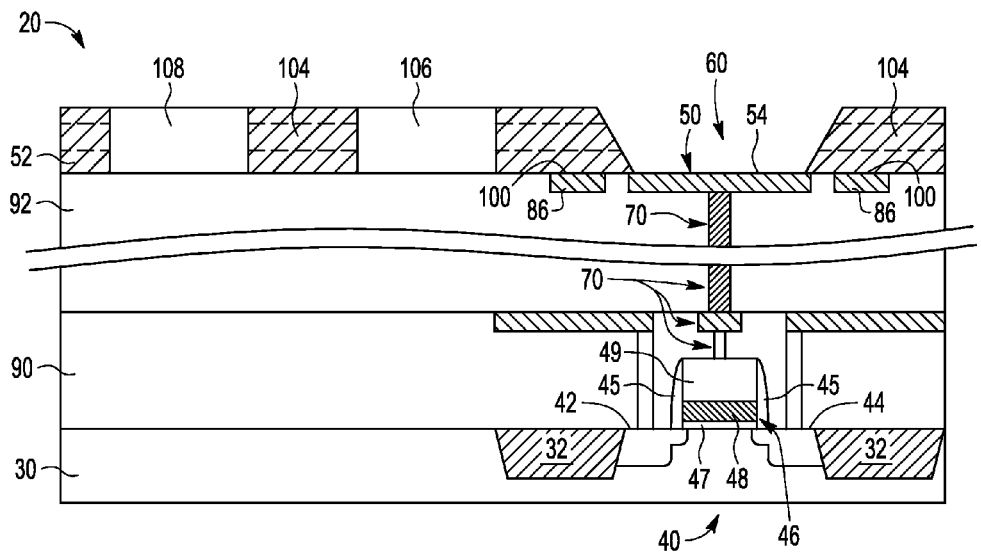
FIG. 22 is a schematic side view of a portion of a process flow for fabrication of a sensor field effect transistor.

Forming the selection structure at 270 can include forming any suitable selection structure on, above, or in, the semiconductor substrate in any suitable manner and is illustrated in FIG. 22 at 108. As an example, and as discussed herein, the SFET can include a plurality of separate, distinct, or spaced apart analyte-receiving regions. Under these conditions, the SFET can be configured to simultaneously provide the analyte fluid to each of the plurality of analyte-receiving regions. Alternatively, the SFET also can be configured to selectively provide the analyte fluid to a given one, or to a subset, of the plurality of analyte-receiving regions. Under these conditions the SFET can include the selection structure and the selection structure can be configured to permit selective flow of the analyte fluid to the given one of the plurality of analyte-receiving regions while restricting flow of the analyte fluid to a remainder of the plurality of analyte-receiving regions. Examples of the selection structure are disclosed herein.

The forming at 270 can be performed in any suitable manner or utilizing any suitable process or processes. As examples, the forming at 270 can include performing one or more of a deposition process, a sputter process, a crystal growth process, a diffusion process, an implant process, an annealing process, a polish process, a lithography process, a damascene process, a wet etch process, and a dry etch process.

Figure 23:
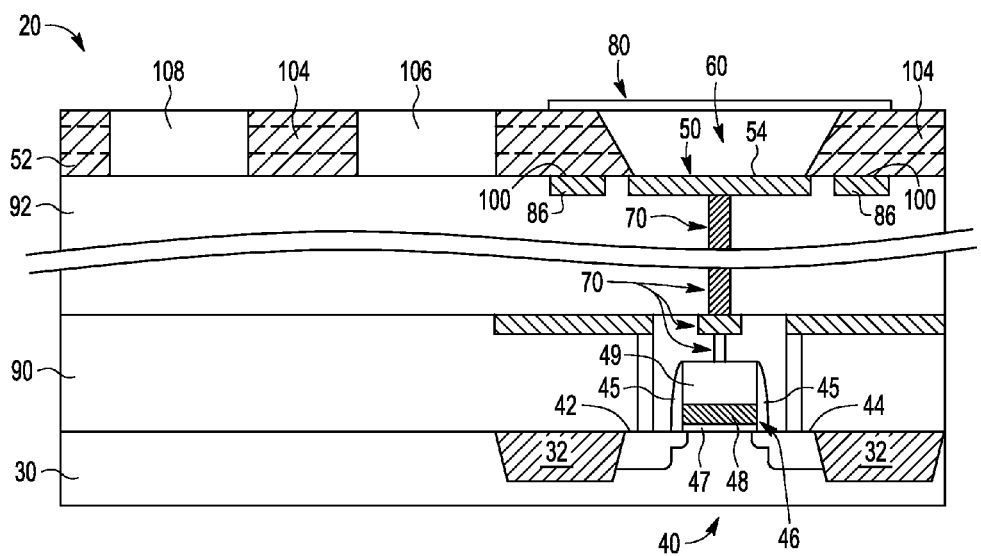
FIG. 23 is a schematic side view of a portion of a process flow for fabrication of a sensor field effect transistor.

FIGS. 21-23 illustrate microfluidic separation structure 106 and selection structure 108 as being formed within or extending within overlaying layer 52. However, this is not required in all embodiments. As examples, microfluidic separation structure 106 or selection structure 108 can be formed or can extend above or below overlaying layer 52.

Placing the cover structure at 280 can include placing any suitable cover structure on the semiconductor substrate such that the cover structure at least partially covers, encloses, surrounds, or encapsulates the analyte-receiving region and is illustrated in FIG. 23 at 80. It is within the scope of embodiments of the present invention that the placing at 280 can include placing in any suitable manner. As an example, the placing at 280 can include attaching a pre-formed, or pre-defined, cover structure on the overlying layer. As another example, the placing at 280 also can include performing a non-conformal deposition process to deposit a cover material at least partially within the analyte-receiving region such that the cover material at least partially encloses the analyte-receiving region. Thus, the placing at 280 also can be referred to herein as locating the cover structure, forming the cover structure, positioning the cover structure, or depositing the cover structure.

The cover structure can be formed from any suitable cover material. As examples, the cover structure can be formed from a dielectric material, silicon oxide, or a glass. As another example, the cover structure can be formed from a soluble cover material that is soluble within the analyte fluid. Under these conditions, and as discussed herein, the cover structure dissolves upon contact with the analyte fluid, thereby permitting the analyte fluid to flow into the analyte-receiving region or to contact the sense electrode.

Although the invention is described herein with reference to specific embodiments, various modifications and changes can be made without departing from the scope of the present invention as set forth in the claims below. As examples, a location, relative orientation, scale, or geometry of the various components of SFETs 20 can vary without departing from the scope of embodiments of the present invention. Accordingly, the specification and Figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any of the claims.

Unless stated otherwise, terms such as "first" and "second" are used to arbitrarily distinguish between the elements such terms describe. Thus, these terms are not necessarily intended to indicate temporal or other prioritization of such elements.

As used herein the terms "adapted" and "configured" mean that the element, component, or other subject matter is designed, or intended, to perform a given function. Thus, the use of the terms "adapted" and "configured" should not be construed to mean that a given element, component, or other subject matter is simply "capable of" performing a given function but that the element, component, or other subject matter is specifically selected, created, implemented, utilized, programmed, or designed for the purpose of performing the function. It is also within the scope of embodiments of the present invention that elements, components, or other recited subject matter that is recited as being adapted to perform a particular function may additionally or alternatively be described as being configured to perform that function, and vice versa.

As used herein, the term "or" should be interpreted as being inclusive or exclusive. For example, "A or B" can be interpreted to mean A, B, or both A and B.

As used herein, the phrase, "for example," the phrase, "as an example," or simply the term "example," when used with reference to one or more components, features, details, structures, embodiments, or methods according to the present disclosure, are intended to convey that the described component, feature, detail, structure, embodiment, or method is an illustrative, non-exclusive example of components, features, details, structures, embodiments, or methods according to the present disclosure. Thus, the described component, feature, detail, structure, embodiment, or method is not intended to be limiting, required, or exclusive/exhaustive; and other components, features, details, structures, embodiments, or methods, including structurally or functionally similar or equivalent components, features, details, structures, embodiments, or methods, are also within the scope of embodiments of the present invention.

The following are various embodiments of the present invention.

In a first embodiment, there is provided a sensor field effect transistor (SFET). The SFET includes a semiconductor substrate and a field effect transistor. The field effect transistor is supported by the semiconductor substrate. The field effect transistor includes a source, a drain, and a gate. The SFET includes a sense electrode. The sense electrode is supported by the semiconductor substrate. The sense electrode is in in electrical communication with the gate. The SFET includes an enclosed analyte channel. The enclosed analyte channel is supported by the semiconductor substrate. The enclosed analyte channel is configured to contain an analyte fluid and to permit fluid contact between the analyte fluid and the sense electrode. The enclosed analyte channel extends in contact with the sense electrode. The enclosed analyte channel extends between an analyte inlet and an analyte outlet. The analyte inlet and the analyte outlet are spaced apart from the sense electrode along a length of the enclosed analyte channel. The SFET can include a microfluidic drive structure. The microfluidic drive structure can be supported by the semiconductor substrate. The microfluidic drive structure can be configured to provide a motive force for flow of the analyte fluid through the enclosed analyte channel. The microfluidic drive structure can include an electroosmotic drive structure. The electroosmotic drive structure can include a plurality of electrical lines. The plurality of electrical lines can be formed across the enclosed analyte channel. The SFET can include a microfluidic separation structure supported by the semiconductor substrate. The microfluidic separation structure can be configured to separate at least one component of the analyte fluid from at least one other component of the analyte fluid prior to fluid contact between the analyte fluid and the sense electrode. The sense electrode can form a portion of the gate. The sense electrode can be spaced apart from the gate and in electrical communication with the gate via an electrode conductor. The SFET can include a trench. The trench can form at least a first portion of the enclosed analyte channel and a cover structure. The cover structure can extend across a portion of an opening of the trench that is opposed to the sense electrode to form at least a second portion of the enclosed analyte channel. The SFET can be configured to convey the analyte fluid between the analyte inlet and the analyte outlet. The SFET can include a soluble inlet cover structure. The soluble inlet cover structure can extend across the analyte inlet and can be formed from a cover material that is soluble within the analyte fluid. The SFET can include a soluble outlet cover structure. The soluble outlet cover structure can extend across the analyte outlet and can be formed from the cover material that is soluble within the analyte fluid. The SFET can include a plurality of spaced apart enclosed analyte channels. Each of the plurality of spaced apart enclosed analyte channels can extend between a respective analyte inlet and a respective analyte outlet. Each of the plurality of spaced apart enclosed analyte channels can extend in contact with the sense electrode. The SFET can include a plurality of spaced apart enclosed analyte channels and a plurality of sense electrodes. Each of the plurality of spaced apart enclosed analyte channels can extend between a respective analyte inlet and a respective analyte outlet. Each of the plurality of spaced apart enclosed analyte channels can extend in contact with a respective sense electrode of the plurality of sense electrodes. Each of the plurality of sense electrodes can be in electrical communication with the gate.

In a second embodiment, there is provided a method of fabricating a sensor field effect transistor (SFET). The SFET can include, or be, the SFET of the first embodiment. The method includes forming a field effect transistor. The field effect transistor includes a source, a drain, and a gate. The field effect transistor is supported by a semiconductor substrate. The method includes forming a sense electrode. The sense electrode is in electrical communication with the gate. The sense electrode is supported by the semiconductor substrate. The method includes forming an overlying layer. The overlying layer extends in contact with the sense electrode. The overlying layer is supported by the semiconductor substrate. The method includes forming an analyte-receiving region within the overlying layer. The analyte-receiving region is configured to contain an analyte fluid. The analyte-receiving region extends in contact with the sense electrode. The analyte-receiving region permits fluid contact between the analyte fluid and the sense electrode. The method includes placing a cover structure on the semiconductor substrate. The cover structure at least partially encloses the analyte-receiving region. The placing the cover structure can include attaching a pre-formed cover structure to the overlying layer. The placing the cover structure can include performing a non-conformal deposition to deposit a cover material at least partially within the analyte-receiving region and to at least partially enclose the analyte-receiving region. The placing the cover structure can include placing a soluble cover material that is soluble in the analyte fluid. The method can include forming a microfluidic drive structure on the semiconductor substrate. The microfluidic drive structure can be configured to provide a motive force for flow of the analyte fluid between an analyte inlet and an analyte outlet of an enclosed analyte channel that comprises the analyte-receiving region. The method can include forming a microfluidic separation structure on the semiconductor substrate. The microfluidic separation structure can be configured to separate at least one component of the analyte fluid from at least one other component of the analyte fluid when the analyte fluid flows through the enclosed analyte channel. The forming the sense electrode can include forming the sense electrode at least partially concurrently with the forming the field effect transistor. The forming the sense electrode can include forming the sense electrode subsequent to the forming the field effect transistor.

In a third embodiment, there is provided a sensor field effect transistor (SFET). The SFET includes a semiconductor substrate. The SFET includes a field effect transistor supported by the semiconductor substrate. The field effect transistor includes a source, a drain, and a gate. The SFET includes a sense electrode supported by the semiconductor substrate. The sense electrode is in electrical communication with the gate. The SFET includes an analyte-receiving region. The analyte-receiving region is supported by the semiconductor substrate and extends in contact with the sense electrode. The analyte-receiving region is configured to receive an analyte fluid. The analyte-receiving region is configured to permit fluid contact between the sense electrode and the analyte fluid. The SFET includes a cover structure. The cover structure at least partially encloses the analyte-receiving region. The cover structure is formed from a cover material that is soluble in the analyte fluid. The analyte-receiving region can form an enclosed analyte channel. The enclosed analyte channel can extend between an analyte inlet and an analyte outlet. The analyte inlet and the analyte outlet can be spaced apart from the sense electrode. The cover structure can include a soluble inlet cover structure. The soluble inlet cover structure can extend across the analyte inlet. The soluble inlet cover structure can be formed from a cover material that is soluble within the analyte fluid. The cover structure can include a soluble outlet cover structure. The soluble outlet cover structure can extend across the analyte outlet. The soluble outlet cover structure can be formed from the cover material that is soluble within the analyte fluid.

What is claimed is:

1. A sensor field effect transistor (SFET), comprising:
   a semiconductor substrate;
   a field effect transistor supported by the semiconductor substrate and comprising a source, a drain, and a gate;
   a sense electrode supported by the semiconductor substrate and in electrical communication with the gate; and
   an enclosed analyte channel that is supported by the semiconductor substrate, is configured to contain an analyte fluid and to permit fluid contact between the analyte fluid and the sense electrode, extends in contact with the sense electrode, and extends between an analyte inlet and an analyte outlet, wherein the analyte inlet and the analyte outlet are spaced apart from the sense electrode along a length of the enclosed analyte channel, wherein the SFET is configured to convey the analyte fluid between the analyte inlet and the analyte outlet, and further wherein the SFET comprises at least one of:
   (i) a soluble inlet cover structure, which extends across the analyte inlet and is formed from a cover material that is soluble within the analyte fluid; and
   (ii) a soluble outlet cover structure, which extends across the analyte outlet and is formed from the cover material.

2. The SFET of claim 1, further comprising a microfluidic drive structure supported by the semiconductor substrate and configured to provide a motive force for flow of the analyte fluid through the enclosed analyte channel.

3. The SFET of claim 2, wherein the microfluidic drive structure comprises an electroosmotic drive structure.

4. The SFET of claim 3, wherein the electroosmotic drive structure comprises a plurality of electrical lines formed across the enclosed analyte channel.

5. The SFET of claim 1, further comprising a microfluidic separation structure supported by the semiconductor substrate and configured to separate at least one component of the analyte fluid from at least one other component of the analyte fluid prior to fluid contact between the analyte fluid and the sense electrode.

6. The SFET of claim 1, wherein the sense electrode forms a portion of the gate.

7. The SFET of claim 1, wherein the sense electrode is spaced apart from the gate and in electrical communication with the gate via an electrode conductor.

8. The SFET of claim 1, further comprising a trench, which forms at least a first portion of the enclosed analyte channel, and a cover structure, which extends across a portion of an opening of the trench that is opposed to the sense electrode to form at least a second portion of the enclosed analyte channel.

9. The SFET of claim 1, wherein the SFET comprises:
   a plurality of spaced apart enclosed analyte channels, wherein
      each of the plurality of spaced apart enclosed analyte channels extends between a respective analyte inlet and a respective analyte outlet, and
      each of the plurality of spaced apart enclosed analyte channels extends in contact with the sense electrode.

10. The SFET of claim 1, wherein the SFET comprises:
    a plurality of spaced apart enclosed analyte channels; and
    a plurality of sense electrodes, wherein
       each of the plurality of spaced apart enclosed analyte channels extends between a respective analyte inlet and a respective analyte outlet,
       each of the plurality of spaced apart enclosed analyte channels extends in contact with a respective sense electrode of the plurality of sense electrodes, and
       each of the plurality of sense electrodes is in electrical communication with the gate.

11. A method of fabricating a sensor field effect transistor (SFET), the method comprising:
    forming a field effect transistor, wherein the field effect transistor comprises a source, a drain, and a gate and is supported by a semiconductor substrate;
    forming a sense electrode, wherein the sense electrode is in electrical communication with the gate and is supported by the semiconductor substrate;
    forming an overlying layer, wherein the overlying layer is in contact with the sense electrode and is supported by the semiconductor substrate;
    forming an analyte-receiving region, which is configured to contain an analyte fluid, within the overlying layer, wherein the analyte-receiving region extends in contact with the sense electrode and permits fluid contact between the analyte fluid and the sense electrode;
    placing a cover structure, which at least partially encloses the analyte-receiving region, on the semiconductor substrate to define an enclosed analyte channel that extends between an analyte inlet and an analyte outlet, wherein the analyte inlet and the analyte outlet are spaced apart from the sense electrode along a length of the enclosed analyte channel, wherein the SFET is configured to convey the analyte fluid between the analyte inlet and the analyte outlet, and further wherein the method comprises at least one of:
  (i) placing a soluble inlet cover across the analyte inlet, wherein the soluble inlet cover is formed from a soluble cover material that is soluble within the analyte fluid; and
  (ii) placing a soluble outlet cover across the analyte outlet, wherein the soluble outlet cover is formed from the soluble cover material.

12. The method of claim 11, wherein the placing the cover structure comprises attaching a pre-formed cover structure to the overlying layer.

13. The method of claim 11, wherein the placing the cover structure comprises performing a non-conformal deposition to deposit a cover material at least partially within the analyte-receiving region and to at least partially enclose the analyte-receiving region.

14. The method of claim 11, wherein the placing the cover structure comprises placing the soluble cover material that is soluble in the analyte fluid.

15. The method of claim 11, wherein the method comprises forming a microfluidic drive structure on the semiconductor substrate, wherein the microfluidic drive structure is configured to provide a motive force for flow of the analyte fluid between the analyte inlet and the analyte outlet of the enclosed analyte channel.

16. The method of claim 11, wherein the method comprises forming a microfluidic separation structure on the semiconductor substrate, wherein the microfluidic separation structure is configured to separate at least one component of the analyte fluid from at least one other component of the analyte fluid when the analyte fluid flows through the enclosed analyte channel.

17. The method of claim 11, wherein the forming the sense electrode comprises at least one of (i) forming the sense electrode at least partially concurrently with the forming the field effect transistor; and (ii) forming the sense electrode subsequent to the forming the field effect transistor.

18. A sensor field effect transistor (SFET), comprising:
  a semiconductor substrate;
  a field effect transistor supported by the semiconductor substrate and comprising a source, a drain, and a gate;
  a sense electrode supported by the semiconductor substrate and in electrical communication with the gate;
  an analyte-receiving region supported by the semiconductor substrate, extending in contact with the sense electrode, and configured to receive an analyte fluid and to permit fluid contact between the analyte fluid and the sense electrode; and
  a cover structure that at least partially encloses the analyte-receiving region, wherein the cover structure is formed from a cover material that is soluble in the analyte fluid, wherein the analyte-receiving region forms an enclosed analyte channel that extends between an analyte inlet and an analyte outlet such that the analyte inlet and the analyte outlet are spaced apart from the sense electrode, and further wherein the cover structure comprises at least one of:
  (i) a soluble inlet cover structure, which extends across the analyte inlet and is formed from a cover material that is soluble within the analyte fluid; and
  (ii) a soluble outlet cover structure, which extends across the analyte outlet and is formed from the cover material.

* * * * *